US006316238B1

(12) United States Patent
Nakamura et al.

(10) Patent No.: US 6,316,238 B1
(45) Date of Patent: Nov. 13, 2001

(54) PROCESS FOR PRODUCING ACTIVATED HUMAN ALT

(75) Inventors: Atsuo Nakamura, Osaka-fu; Toshio Tanaka, Toyko; Yushi Matsuo, Osaka-fu; Sumio Tanase, Kumamoto-ken; Masahiko Funatsu, Kumamoto-ken; Akira Eto, Kumamoto-ken, all of (JP)

(73) Assignee: Oriental Yeast Co., Ltd., Tokyo (JP)

( * ) Notice: Subject to any disclaimer, the term of this patent is extended or adjusted under 35 U.S.C. 154(b) by 0 days.

(21) Appl. No.: 09/142,481

(22) PCT Filed: Sep. 19, 1997

(86) PCT No.: PCT/JP97/03339

§ 371 Date: Sep. 9, 1998

§ 102(e) Date: Sep. 9, 1998

(87) PCT Pub. No.: WO98/30703

PCT Pub. Date: Jul. 16, 1998

(30) Foreign Application Priority Data

Jan. 9, 1997 (JP) .................................................. 9-013282

(51) Int. Cl.$^7$ ............................... C12N 9/10; C12N 1/21; C12N 15/52; C07H 21/04
(52) U.S. Cl. ................. 435/193; 435/252.3; 435/252.33; 435/320.1; 536/23.2
(58) Field of Search ............................. 435/252.3, 320.1, 435/193; 536/23.2

(56) References Cited

U.S. PATENT DOCUMENTS 5,952,211 * 11/1999 Nakamura et al. ................... 435/193

FOREIGN PATENT DOCUMENTS

| 5068548 | 3/1993 | (JP) . |
| 08103278 | 4/1996 | (JP) . |

OTHER PUBLICATIONS

Ishiguro, M., et al., "Complete Amino Acid Sequence of Human Liver Cytosolic Alanine Aminotransferase (GPT) Determined by a Combination of Conventional and Mass Spectral Methods," *Biochemistry* 30:10451–10457 (1991).
Ishiguro, M., et al., "Complete Amino Acid Sequence of Rat Liver Cytosolic Alanine Aminotransferase," *Biochemistry* 30:6048–6053 (1991).
Itakura, K., et al., "Expression in *Escherichia coli* of a Chemically Synthesized Gene for the Hormone Somatostatin," *Science* 198:1056–1063 (1977).
Saito, H., et al., "Preparation of Transforming Deoxyribonucleic Acid by Phenol Treatment," *Biochim. Biophys. Acta.* 72:619–629 (1963).
Dugsiczyk, A., et al., "Ligation of EcoRI Endonuclease–generated DNA Fragments into Linear and Circular Structures," *J. Mol. Biol.* 96:171–184 (1975).

Chung, C.T., et al., "One–step Preparation of Competent *Escherichia coli*: Transformation and Storage of Bacterial Cells in the Same Solution," *Proc. Natl. Acad. Sci. USA* 86:2172–2175 (1989).
Birnboim, H.C., et al., "A Rapid Extraction Procedure for Screening Recombinant Plasmid DNA," *Nucleic Acids Research* 7–6:1513–1523 (1979).
Kanemitsu, F., et al., "Electrophoretic and Kinetic Characterization of Three Variants of Soluble Cytoplasmic L–Alanine:2–Oxoglutarate Aminotransferase in Human Liver Tissue," *Clin. Biochem.* 23:121–125 (1990).
Japanese Journal of Clinical Chemistry, vol. 25 supp. 3 (1996).
Skoog, B., et al., "Calculation of the Isoelectric Points of Polypeptides from the Amino Acid Composition," *Trends in Analytical Chemistry* 5–4:82–83 (1986).
Devlin, P.E. et al., "Alteration of Amino–Terminal Codons of Human Granulocyte–Colony–Stimulating Factor Increases Expression Levels and Allows Efficient Processing by Methionine Aminopeptidase in *Escherichia coli*," *Gene* 65:13–22 (1988).
Reznikoll, W., et al., "Maximizing Gene Expression," Chapter 7, Stormo, G.D., "Translation Initiation," Butterworth Publishers pp. 195, 206–208 (1986).
Goeddel, D.V. "Methods in Enzymology vol. 185, Gene Expression Technology," Balbas, P., et al., "Design and Construction of Expression Plasmid Vectors in *Escherichia coli*," pp. 14–37 (1990).
Goeddel, D.V., "Methods in Enzymology vol. 185, Gene Expression Technology," Schoner, B.E., et al, Enhanced Translational Efficiency with Two–Cistron Expression System, pp. 94–103 (1990).
Cohen, P., "The Role of Protein Phosphorylation in Neural and Hormonal Control of Cellular Activity," *Nature* 296:613–620 (1982).
Sambrook, J., et al., "Molecular Cloning: A Laboratory Manual, Second Edition," Cold Spring Harbor Laboratory Press, Section 17.20–17.24 (1989).
Laemmli, U.K., "Cleavage of Structural Proteins During the Assembly of the Head of Bacteriophage T4," *Nature* 227:680–685 (1970).

* cited by examiner

Primary Examiner—Elizabeth Slobodyansky
(74) *Attorney, Agent, or Firm*—Browdy and Neimark

(57) ABSTRACT

The present invention relates to an altered-type human ALT gene in which the codons for the five amino acids in the human ALT (alanine aminotransferase) gene are replaced, i. e. the fourth amino acid codon from the initiation codon for methionine (Met) is replaced by a codon for serine (Ser), the fifth by a codon for threonine (Thr), the seventh by a codon for aspartic acid (Asp), the 39th by a codon for glycine (Gly) and the 222nd by a codon for alanine (Ala), and concurrently, restriction sites are added at the upstream and downstream of said gene.

The active human ALT having properties similar to those of the native enzyme can be effectively produced by culturing *E. coli* transformed with a recombinant plasmid in which the altered-type human ALT gene of the present invention is ligated to a vector.

14 Claims, 9 Drawing Sheets

FIG. 1

TOTAL NUCLEOTIDE SEQUENCE OF HUMAN ALT

```
              10        20        30        40        50        60
         GAATTCATATGGCAAGCTCAACAGGTGATAGATCTCAGGCGGTGAGGCATGGACTGAGGG
                    M  A  S  S  T  G  D  R  S  Q  A  V  R  H  G  L  R  A 70        80        90       100       110       120
         CGAAGGTGCTGACGCTGGACGGCATGAACCCGCGTGTGCGGAGAGTGGAGTACGCAGTGC
          K  V  L  T  L  D  G  M  N  P  R  V  R  R  V  E  Y  A  V  R 130       140       150       160       170       180
         GTGGGCCCATAGTGCAGCGAGCCTTGGAGCTGGAGCAGGAGCTGCGCCAGGGTGTGAAGA
          G  P  I  V  Q  R  A  L  E  L  E  Q  E  L  R  Q  G  V  K  K 190       200       210       220       230       240
         AGCCTTTCACCGAGGTCATCCGTGCCAACATCGGGGACGCACAGGCTATGGGGCAGAGGC
           P  F  T  E  V  I  R  A  N  I  G  D  A  Q  A  M  G  Q  R  P 250       260       270       280       290       300
         CCATCACCTTCCTGCGCCAGGTCTTGGCCCTCTGTGTTAACCCTGATCTTCTGAGCAGCC
           I  T  F  L  R  Q  V  L  A  L  C  V  N  P  D  L  L  S  S  P 310       320       330       340       350       360
         CCAACTTCCCTGACGATGCCAAGAAAAGGGCGGAGCGCATCTTGCAGGCGTGTGGGGGCC
           N  F  P  D  D  A  K  K  R  A  E  R  I  L  Q  A  C  G  G  H 370       380       390       400       410       420
         ACAGTCTGGGGGCCTACAGCGTCAGCTCCGGCATCCAGCTGATCCGGGAGGACGTGGCGC
           S  L  G  A  Y  S  V  S  S  G  I  Q  L  I  R  E  D  V  A  R 430       440       450       460       470       480
         GGTACATTGAGAGGCGTGACGGAGGCATCCCTGCGGACCCCAACAACGTCTTCCTGTCCA
           Y  I  E  R  R  D  G  G  I  P  A  D  P  N  N  V  F  L  S  T 490       500       510       520       530       540
         CAGGGGCCAGCGATGCCATCGTGACGGTGCTGAAGCTGCTGGTGGCCGGCGAGGGCCACA
           G  A  S  D  A  I  V  T  V  L  K  L  L  V  A  G  E  G  H  T
```

FIG. 2

```
        550        560        570        580        590        600
CACGCACGGGTGTGCTCATCCCCATCCCCCAGTACCCACTCTACTCGGCCACGCTGGCAG
  R   T   G   V   L   I   P   I   P   Q   Y   P   L   Y   S   A   T   L   A   E 610        620        630        640        650        660
AGCTGGGCGCAGTGCAGGTGGATTACTACCTGGACGAGGAGCGTGCCTGGGCGCTGGACG
  L   G   A   V   Q   V   D   Y   Y   L   D   E   E   R   A   W   A   L   D   V 670        680        690        700        710        720
TGGCCGAGCTTGCTAGGGCTCTGGGCCAGGCGCGTGACCACTGCCGCCCTCGTGCGCTCT
  A   E   L   A   R   A   L   G   Q   A   R   D   H   C   R   P   R   A   L   C 730        740        750        760        770        780
GTGTCATCAACCCTGGCAACCCCACCGGGCAGGTGCAGACCCGCGAGTGCATCGAGGCCG
  V   I   N   P   G   N   P   T   G   Q   V   Q   T   R   E   C   I   E   A   V 790        800        810        820        830        840
TGATCCGCTTCGCCTTCGAAGAGCGGCTCTTTCTGCTGGCGGACGAGGTGTACCAGGACA
  I   R   F   A   F   E   E   R   L   F   L   L   A   D   E   V   Y   Q   D   N 850        860        870        880        890        900
ACGTGTACGCCGCGGGTTCGCAGTTCCACTCATTCAAGAAGGTGCTCATGGAGATGGGGC
  V   Y   A   A   G   S   Q   F   H   S   F   K   K   V   L   M   E   M   G   P 910        920        930        940        950        960
CGCCCTACGCCGGGCAGCAGGAGCTTGCCTCCTTCCACTCCACCTCCAAAGGCTACATGG
  P   Y   A   G   Q   Q   E   L   A   S   F   H   S   T   S   K   G   Y   M   G 970        980        990       1000       1010       1020
GCGAGTGCGGGTTCCGCGGCGGCTATGTGGAGGTGGTGAACATGGACGCTGCAGTGCAGC
  E   C   G   F   R   G   G   Y   V   E   V   V   N   M   D   A   A   V   Q   Q 1030       1040       1050       1060       1070       1080
AGCAGATGCTGAAGCTGATGAGTGTGCGGCTGTGCCCGCCGGTGCCAGGACAGGCCCTGC
  Q   M   L   K   L   M   S   V   R   L   C   P   P   V   P   G   Q   A   L   L 1090       1100       1110       1120       1130       1140
TGGACCTGGTGGTCAGCCCGCCCGCGCCCACCGACCCCTCCTTTGCGCAGTTCCAGGCTG
  D   L   V   V   S   P   P   A   P   T   D   P   S   F   A   Q   F   Q   A   E
```

FIG. 3

```
        1150       1160       1170       1180       1190       1200
AGAAGCAGGCAGTGCTGGCAGAGCTGGCGGCCAAGGCCAAGCTCACCGAGCAGGTCTTCA
  K   Q   A   V   L   A   E   L   A   A   K   A   K   L   T   E   Q   V   F   N 1210       1220       1230       1240       1250       1260
ATGAGGCTCCTGGCATCAGCTGCAACCCAGTGCAGGGCGCCATGTACTCCTTCCCGCGCG
  E   A   P   G   I   S   C   N   P   V   Q   G   A   M   Y   S   F   P   R   V 1270       1280       1290       1300       1310       1320
TGCAGCTGCCCCCGCGGGCGGTGGAGCGCGCTCAGGAGCTGGGCCTGGCCCCCGATATGT
  Q   L   P   P   R   A   V   E   R   A   Q   E   L   G   L   A   P   D   M   F 1330       1340       1350       1360       1370       1380
TCTTCTGCCTGCGCCTCCTGGAGGAGACCGGCATCTGCGTGGTGCCAGGGAGCGGCTTTG
  F   C   L   R   L   L   E   E   T   G   I   C   V   V   P   G   S   G   F 1390       1400       1410       1420       1430       1440
GGCAGCGGGAAGGCACCTACCACTTCCGGATGACCATTCTGCCCCCCTTGGAGAAACTGC
  Q   R   E   G   T   Y   H   F   R   M   T   I   L   P   P   L   E   K   L   R 1450       1460       1470       1480       1490       1500
GGCTGCTGCTGGAGAAGCTGAGCAGGTTCCATGCCAAGTTCACCCTCGAGTACTCCTGA G
  L   L   L   E   K   L   S   R   F   H   A   K   F   T   L   E   Y   S   *
```

<u>GATCC</u>

NOTE: The underlined parts show altered bases and amino acid residues.

FIG. 4

```
PF4 - 11        1        4   5      7
                MetAlaSerSerThrGlyAspAr
5' -GGGAATTCATATGGCAAGCTCAACAGGTGATAG
          EcoRI gSerGlnAlaValArgHis
    ATCTCAGGCGGTGAGGCATGG- 3'

PFA - 1                     ApaI
3' - ACCTCATGCGTCACGCACCCGGGTAT-5'
        GluTyrAlaValArgGlyProIle
                           39

PF11
5' - CGTGGGCCCATAGTGCAGCGAGCCTTG-3'
          ApaI

PFA - 11
3'  - GGTTGAAGGGACTGCTACGGTT-5'

PF21
5' - CTGGAATTCCCCAACTTCCCTGACGATGCC-3'
          EcoRI

PFA - 21                            StuI
3' - CGCGACCTGCACCGGCTCGAACGATCCGGAGAC
-5'    AlaLeuAspValAlaGluLeuAlaArg
                                222

PF31
5' - CACAGCGCTCTGGGCCAGGCGCGTGAC-3'

PFA-41
3' - CAAGGTACGGTTCAAGTGGGAGCTCATGAGGAC

TCCTAGGGG - 5'
         BamHI
```

FIG. 8

TOTAL BASE SEQUENCE OF pTRP (2927 bp)

```
   1  AGCGCCCAAT ACGCAAACCG CCTCTCCCCG CGCCGTTGGCC GATTCATTAA TGCAGCTGGC
  61  ACGACAGTT TCCCGACTGG AAAGCGGGCA GTGAGCGCAA CGCAATTAAT GTGAGTTAGC
 121  TCACTCATTA GGCACCCCAG GCTTTACACT TTATGCTTCC GGCTCGTATG TTGTGTGGAA
 181  TTGTGAGCGG ATAACAATTT CACACAGGAA ACAGCTATGA CCATGATTAC GCCAAGCTCT
```
<span style="writing-mode: vertical-rl;">TRP PROMOTER DERIVED FROM E. coli K12 STRAIN</span>

```
 241  AATACGACTC ACTATAGGGA AAGCTT      CCCTGTTGACAATTAATCATGAACTAGTTAAC
                                 HindIII
 300  AGTACGCAAGTTCACGTAAAAAGGGTA      GAATTCGAGCTCGGTACCCGGGGATCCTCTAGA
           PstI                          EcoRI                    BamHI
 360  GTCGACCTGCAGGTCGAAATTC ACTGGCCCG TCGTTTTACA ACGTCGTGAC TGGGAAAACC
 420  CTGGCGTTAC CCAACTTAAT CGCCTTGCAG CACATCCCCC TTTCGCCAGC TGGCGTAATA
 480  GCGAAGAGGC CCGCACCGAT CGCCCTTCCC AACAGTTGCG CAGCCTGAAT GGCGAATGGG
 540  ACGCGCCCTG TAGCGGCGCA TTAAGCGCGG CGGGTGTGGT GGTTACGCGC AGCGTGACCG
 600  CTACACTTGC CAGCGCCCTA CCGCCCGCTC CTTTCGCTTT CTTCCCTTCC TTTCTCGCCA
 660  CGTTCGCCGG CTTTCCCCGT CAAGCTCTAA ATCGGGGGCT CCCTTTAGGG TTCCGATTTA
 720  GTGCTTTACG GCACCCTCGAC CCCAAAAAAC TTGATTAGGG TGATGGTTCA CGTAGTGGGC
 780  CATCGCCCTG ATAGACGGTT TTTCGCCCTT TGACGTTGGA GTCCACGTTC TTTAATAGTG
 840  GACTCTTGTT CCAAACTGGA ACAACACTCA ACCCTATCTC GGTCTATTCT TTTGATTTAT
 900  AAGGGATTTT GCCGATTTCG GCCTATTGGT TAAAAAATGA GCTGATTTAA CAAAAATTTA
 960  ACGCGAATTT TAACAAAATA TTAACGTTTA CAATTTCAGG TGCACTTTT CGGGGAAATG
1020  TGCGCGGAAC CCCTATTTGT TTATTTTTCT AAATACATTC AAATATGTAT CCGCTCATGA
1080  GACAATAACC CTGATAAATG CTTCAATAAT ATTGAAAAAG GAAGAGTATG AGTATTCAAC
1140  ATTTCCGTGT CGCCCTTATT CCCTTTTTTG CGGCATTTTG CCTTCCTGTT TTTGCTCACC
1200  CAGAAACGCT GGTGAAACTA AAAGATGCTG AAGATCAGTT GGGTGCACGA GTGGGTTACA
1260  TCGAACTGGA TCTCAACAGC GGTAAGATCC TTGAGAGTTT TCGCCCCGAA GAACGTTTTC
```
<span style="writing-mode: vertical-rl;">INITIATION CODON OF B-LACTAMASE</span>

FIG. 9

| | | | | | | |
|---|---|---|---|---|---|---|
|1320|CAATGATGAG|CACTTTTAAA|GTTCTGCTAT|GTGGCGCGGT|ATTATCCCGT|ATTGACGCCG|
|1380|GGCAAGAGCA|ACTCGGTCGC|CGCATACACT|ATTCTCAGAA|TGACTTGGTT|GAGTACTCAC|
|1440|CAGTCACAGA|AAAGCATCTT|ACGGATGGCA|TGACAGTAAG|AGAATTATGC|AGTGCTGCCA|
|1500|TAACCATGAG|TGATAACACT|GCGGCCAACT|TACTTCTGAC|AACGATCGGA|GGACCGAAGG|
|1560|AGCTAACCGC|TTTTTTGCAC|AACATGGGGG|ATCATGTAAC|TCGCCTTGAT|CGTTGGGAAC|
|1620|CGGAGCTGAA|TGAAGCCATA|CCAAACGACG|AGCGTGACAC|CACGATGCCT|GTAGCAATGG|
|1680|CAACAACGTT|GCGCAAACTA|TTAACTGGCG|AACTACTTAC|TCTAGCTTCC|CGGCAACAAT|
|1740|TAATAGACTG|GATGGAGGCG|GATAAAGTTG|CAGGACCACT|TCTGCGCTCG|GCCCTTCCGG|
|1800|CTGGCTGGTT|TATTGCTGAT|AAATCTGGAG|CCGGTGAGCG|TGGGTCTCGC|GGTATCATTG|
|1860|CAGCACTGGG|GCCAGATGGT|AAGCCCTCCC|GTATCGTAGT|TATCTACACG|ACGGGGAGTC|
|1920|AGGCAACTAT|GGATGAACGA|AATAGACAGA|TCGCTGAGAT|AGGTGCCTCA|CTGATTAAGC|
|1980|ATTGGTAACT|GTCAGACCAA|GTTTACTCAT|ATATACTTTA|GATTGATTA|AAACTTCATT| TERMINATION CODON OF B-LACTAMASE
|2040|TTTAATTTAA|AAGGATCTAG|GTGAAGATCC|TTTTTGATAA|TCTCATGACC|AAAATCCCTT|
|2100|AACGTGAGTT|TTCGTTCCAC|TGAGCGTCAG|ACCCCGTAGA|AAAGATCAAA|GGATCTTCTT|
|2160|GAGATCCTTT|TTTTCTGCGC|GTAATCTGCT|GCTTGCAAAC|AAAAAAACCA|CCGCTACCAG|
|2220|CGGTGGTTTG|TTTGCCGGAT|CAAGAGCTAC|CAACTCTTTT|TCCGAAGGTA|ACTGGCTTCA|
|2280|GCAGAGCGCA|GATACCAAAT|ACTGTCCTTC|TAGTGTAGCC|GTAGTTAGGC|CACCACTTCA|
|2340|AGAACTCTGT|AGCACCGCCT|ACATACCTCG|CTCTGCTAAT|CCTGTTACCA|GTGGCTGCTG|
|2400|CCAGTGGCGA|TAAGTCGTGT|CTTACCGGGT|TGGACTCAAG|ACGATAGTTA|CCGGATAAGG|
|2460|CGCAGCGGTC|GGGCTGAACG|GGGGGTTCGT|GCACACAGCC|CAGCTTGGAG|CGAACGACCT|
|2520|ACACCGAACT|GAGATACCTA|CAGCGTGAGC|ATTGAGAAAG|CGCCACGCTT|CCCGAAGGGA|
|2580|GAAAGGCGGA|CAGGTATCCG|GTAAGCGGCA|GGGTCGGAAC|AGGAGAGCGC|ACGAGGGAGC|
|2640|TTCCAGGGGG|AAACGCCTGG|TATCTTTATA|GTCCTGTCGG|GTTTCGCCAC|CTCTGACTTG|
|2700|AGCGTCGATT|TTTGTGATGC|TCGTCAGGGG|GGCGGAGCCT|ATGGAAAAAC|GCCAGCAACG|
|2760|CGGCCTTTTT|ACGGTTCCTG|GCCTTTTGCT|GGCCTTTTGC|TCACATGTTC|TTTCCTGCGT|
|2820|TATCCCCTGA|TTCTGTGGAT|AACCGTATTA|CCGCCTTTGA|GTGAGCTGAT|ACCGCTCGCC|
|2880|GCAGCCGAAC|GACCGAGCGC|AGCGAGTCAG|TGAGCGAGGA|AGCGGAAG| |

PROCESS FOR PRODUCING ACTIVATED HUMAN ALT

BACKGROUND OF THE INVENTION

Field of the Invention

The present invention relates to the production of a human ALT (alanine aminotransferase), and particularly, an active human ALT maintaining a sufficient enzyme activity and having a similar property to that of the native enzyme.

More precisely, the present invention relates to a novel gene encoding an amino acid sequence of a human ALT, a novel plasmid having an altered-type human ALT gene having restriction sites added at the upstream and downstream of said gene, and *Escherichia coli* transformed with said plasmid, as well as a process for production in which the human ALT is expressed as an active enzyme using said *Escherichia coli*.

DESCRIPTION ON THE RELATED ART

Human ALT is an enzyme that is leaked into serum in liver diseases such as viral hepatitis, hepatic cirrhosis and the like, and is important in clinical chemistry. In the serum diagnosis, standardization such as minimization of the difference between laboratories on measured values of ALT activity and the like is one of important problems. While a crude product originated from porcine heart is presently used as the standard for such purpose, this product is different from human enzyme in enzymological properties such as substrate specificity, Km values and the like, and therefore, there has been a demand for commercialization of an active enzyme originated from human.

On the other hand, the production of a protein derived from a heterologous organism in a microorganism became possible and it has been put to the practical application, thanks to the recent genetic engineering technology. For example, the production of an animal protein in *Escherichia coli* into which a plasmid formed by ligating a lactose promoter to plasmid pBR 322 is introduced is described in Science, 198, 1056, 1978. While, in the case of human ALT, the gene is cloned and its expression in *Escherichia coli* is attempted, there has not been an article reporting the expression of the ALT protein maintaining a sufficient activity.

The present inventors have also attempted previously the expression of a recombinant human ALT as an active holoenzyme in *Escherichia coli*, but fails to successfully obtain a high expression of the desired recombinant enzyme (Japanese Patent Publication (A) Hei 8-103278).

In the field of clinical laboratory test, standardization such as minimization of the difference between laboratories on measured values of ALT activity and the like is one of important problems. While a crude product originated from porcine heart is presently used as the standard for such purpose, this product is different from the human enzyme in enzymological properties such as substrate specificity, Km values and the like. Therefore, there has been a demand for an active enzyme originated from human, but a large supply of the enzyme from human tissues has been difficult.

BRIEF DESCRIPTION OF THE DRAWINGS

FIG. 1 shows a DNA sequence of a human ALT gene according to the present invention (SEQ ID NO:1) and its encoded amino acid sequence (SEQ ID NO:2).

FIG. 2 shows a continuation therefrom.

FIG. 3 shows a continuation therefrom.

FIG. 4 shows primers for PCR.

FIG. 8 shows the total nucleotide sequence (SEQ ID NO:14) of the expression vector PTRP.

FIG. 9 shows a continuation therefrom. As the result of base sequencing, it was found that the open reading frame contained only a structural gene for β-lactamase.

DESCRIPTION OF THE INVENTION

Figure 5:
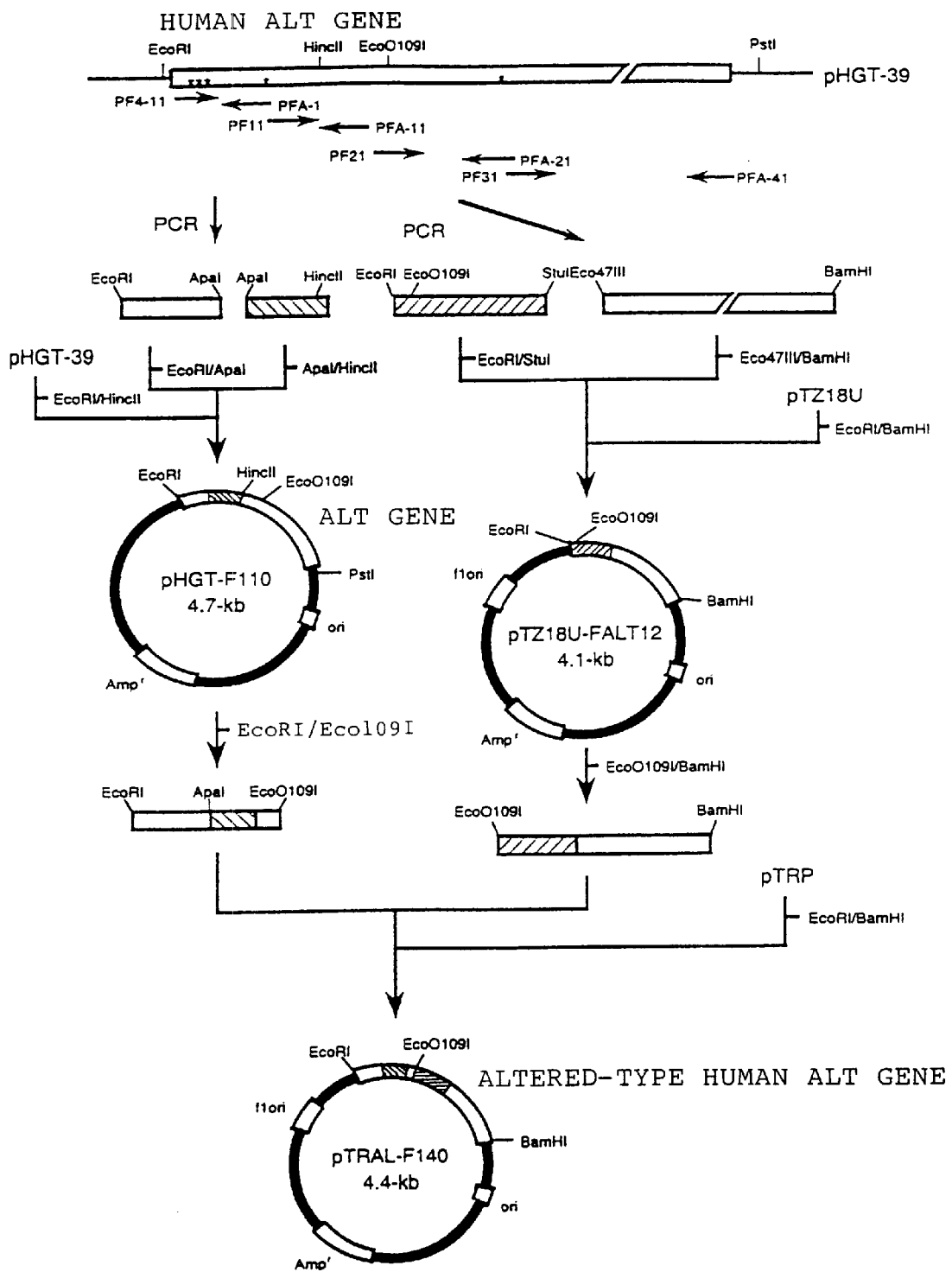
FIG. 5 shows a process for preparing recombinant plasmid pTRAL-F140 of *Escherichia coli* having a human ALT gene altered by PCR.

As the result of studies made from various directions for solving these problems, the present inventors have again paid attention on the previous research, made by the present inventors, in which the expected result was not sufficiently achieved; have desired to solve the problems by modifying/optimizing the nucleotide sequence of the human ALT gene; have conducted extensive studies on specific measure for such purpose; have succeeded in alteration after repeating trial and error; and have successfully confirmed the expression in *Escherichia coli* and also confirmed the fact that the obtained altered-type human ALT is excellent as compared with the above-mentioned human ALT; and thus have completed the present invention.

After studying from various directions a system that allows most effective expression of the altered-type human ALT, the present inventors have first paid attention on the utilization of the previous human ALT gene, and have carried out researches with reference to the amino acid sequence of native human ALT reported by Ishiguro et al. (Biochemistry, 30, 10451–10457, 1991), and finally, have paid attention on five amino acids in the human ALT gene for the first time.

Further, they have confirmed a combination that allows expression of the desired altered-type ALT by replacing codons for these five amino acids, and have newly developed a method that allows effective performance of this replacement, and have first succeeded to develop a total system for industrial production of the altered-type ALT.

Thus, they replaced the codons for the five amino acids in the human ALT gene based on the amino acid sequence of the native human ALT reported by Ishiguro et al., and simultaneously considered about an altered-type human ALT gene having restriction sites added at the upstream and downstream of said gene, a recombinant plasmid in which the altered-type human ALT gene is ligated to a vector plasmid, *Escherichia coli* transformed with said plasmid, and a process for production in which the human ALT is expressed as an active enzyme using the transformed *Escherichia coli*.

First, four kinds of gene fragments were amplified by means of PCR (Polymerase Chain Reaction) using a plasmid containing a cloned gene encoding the human ALT as a template and using eight kinds of primers for replacing the codons for the five amino acids in the human ALT gene. An altered human ALT gene (FIG. 1, FIG. 2 and FIG. 3: SEQ ID NO:1 in SEQUENCE LISTING) was obtained by exchanging a region of human ALT gene with the gene fragments amplified by said PCR, in order to replace the amino acids. Then a plasmid in which the altered-type human ALT gene was introduced was obtained, and *Escherichia coli* transformed by the recombinant plasmid was created. The human ALT was actually expressed as an active enzyme by culturing the transformed *Escherichia coli*, and thus the present invention was completed.

Accordingly, in the present invention is taken a DNA shown by Sequence No. 1 in Sequence Listing as the fundamental technical idea, and more specifically, are obtained a recombinant plasmid formed by replacing the codons for the five specific amino acids in the previously mentioned human ALT gene, preparing concurrently an ALT gene having restriction sites added at the upstream and downstream of said gene and ligating it to a vector plasmid, and *Escherichia coli* transformed with the recombinant plasmid formed by replacing the codons for the five amino acids in the human ALT gene, preparing concurrently an ALT gene having restriction sites added at the upstream and downstream of said gene and ligating it to a vector plasmid, and is collected ALT by culturing the transformant.

The plasmid of the present invention can be prepared, for example, by digesting the human ALT gene, and a DNA having a role as a promoter and a vector with restriction enzymes by the method described in J. Mol. Biol., 96, 171–184, 1974, and then ligating with a ligase, according to the method described in Biochem. Biophys. Acta, 72, 619–629, 1963.

The DNA having a role as a vector includes, for example, DNA's such as pBR 322 derived from *Escherichia coli* and the like. The promoter includes, for example, Tac promoter, tryptophan promoter, lambda PL promoter, lambda PR promoter, lactose promoter, T7 promoter and the like. The restriction enzyme includes, for example, EcoRI and BamHI and the ligase includes, for example, T4 DNA ligase.

The altered-type human ALT gene used in the present invention can be formed by amplifying four kinds of gene fragments by means of PCR using a cloned ALT gene derived from the human liver as a template and using eight kinds of primers for replacing the codons for the five amino acids in the human ALT gene, and exchanging a region of human ALT gene with the gene fragments amplified by said PCR, in order to replace the amino acids. Said eight kinds of primers used here are nucleotide sequences designed for replacing the codons for the five amino acids in the human ALT gene and for adding restriction sites at the upstream and downstream of the gene. Recombinant plasmid pTRAL-F140 for production of human ALT in the cells of *Escherichia coli* can be prepared by introducing the altered-type human ALT gene into expression vector pTRP. A transformant that produces the human ALT in the microbial cells can be obtained by transforming *Escherichia coli* with the recombinant plasmid having the altered-type human ALT gene of the present invention.

The cloned ALT gene derived from the human liver described above includes, for example, plasmid pHGT-39 (FIG. 5). In addition, as the primer, the sequences (FIG. 4), for example, can be used.

By culturing the transformant of *Escherichia coli* prepared in the above described manner under suitable medium conditions, it is possible to produce the human ALT, particularly the active human ALT having a sufficient enzyme activity in a large quantity. Isolation of the human ALT after cultivation can be performed, for example, by disrupting of the cells with a disrupting means such as ultra-sonication or the like, separation and purification.

Utilization of other host vector system, such as those of *Bacillus subtilis*, yeast, Chinese hamster oocyte (CHO) and the like, than the host vector system of *Escherichia coli* is also possible and the mass production of the human ALT can be conducted using these system.

EXAMPLES

The present invention will now be specifically described by means of Examples.

EXAMPLE 1

(a) Amplification of Partial Fragments of an Altered-type Human ALT Gene by PCR

Eight kinds of primers shown in FIG. 4, i.e. PF4-11, PFA-1 (SEQ ID NO:3) (SEQ ID NO:5), PF11 (SEQ ID NO:7), PFA-11 (SEQ ID NO:8), PF21 (SEQ ID NO:9), PFA-21 (SEQ ID NO:10), PF31(SEQ ID NO:12) and PFA-41 (SEQ ID NO:13), were obtained by DNA-synthesizing and four kinds of partial gene fragments were amplified by PCR with PF4-11 and PFA-1, PF11 and PFA-11, -PF21 and PFA-21, and PF31 and PFA-41, respectively, using a pHGT-39 containing a cloned human ALT gene as a template.

Of the above described primers, PF4-11, PF11, PF21 and PF31 were sense primers, PFA-1, PFA-11,. PFA-21 and PFA-41 were antisense primers, and they were designed on the basis of the nucleotide sequence of the human ALT. In the row above PF4-11 (SEQ ID NO:4), and the rows under PFA-1 (SEQ ID NO:6) and PFA-21 (SEQ ID NO:11), amino acid sequences encoded by them are shown. The underlines in nucleotide sequences of primers indicate the replaced bases and added restriction sites. The underlines in the amino acid sequence indicate the amino acid residues replaced by the replaced bases. Thus, primers were prepared according to a nucleotide sequence in which the fourth amino acid codon from the initiation codon for methionine (Met) in the amino acid sequence was replaced by a codon for serine (Ser), the fifth by a codon for threonine (Thr), the seventh by a codon for aspartic acid (Asp), the 39th by a codon for glycine (Gly) and the 222nd by a codon for alanine (Ala), based on the amino acid sequence of the native human ALT reported by Ishiguro et al. The reaction composition for amplification by PCR contained 50 mM KCl, 10 mM Tris-HCl (pH 8.3), 1.5 mM $MgCl_2$, 0.01% (W/V) gelatin, each 100 μM of dNTP, each 0.5 μM of primers, 40 pg of the plasmid (pHGT-39) having the cloned human ALT gene, 100 μl containing 2.5 U of Taq polymerase (manufactured by Perkin Elmer Cetus) and 100 μl of mineral oil to be overlaid.

The reaction conditions included a denaturation step at 94° C. for 1 minute, an annealing step at 55° C. for 1 minute, and a polymerase reaction step at 72° C. for 1 minute and 15 seconds. This incubation was carried out at 35 cycles.

After contaminating protein in the reaction solution was removed by phenol extraction, the DNA fraction containing the PCR amplification products was precipitated by cold ethanol and recovered. Further, the four kinds of the partial fragments of the ALT gene were confirmed by agarose electrophoresis.

(b) Construction of a Human ALT Gene and Preparation of a Recombinant Plasmid pTRAL for the Purpose of its Expression As an expression vector, pTRP of about 2.9 kb having a tryptophan promoter, Shine-Dalgarno sequence (SD sequence), and a multi-cloning site containing ECORI and BamHI was used.

Each 1 μg of gene fragments (PF4-11/PFA-1, PF11/PFA-11, PF21/PFA-21, and PF31/PFA-41) amplified by PCR were digested with combinations of restriction enzymes EcoRI-ApaI, ApaI-HincII, EcoRI-StuI and Eco47III-BamHI (all the restriction enzymes and enzyme reaction solutions theref or were manufactured by Takara Shuzo), respectively, at 37° C. for 2 hours. Respective reaction solutions (100 μl) were subjected to agarose electrophoresis, and the gel sections containing the digested gene partial fragments were excised out, melted at 65° C. and subjected to ethanol precipitation to recover the respective gene partial fragments (123 bp, 153 bp, 385 bp and 822 bp, respectively). Two gene partial fragments, i. e. PF4-11/PFA-1 and PF11/PFA-11, were mixed with pHGT-39 (4.4 kb) digested in advance with EcoRI-HincII and ligated with a DNA ligation kit (manufactured by Takara Shuzo) to give recombinant plasmid pHGT-F110 of 4.7 kb.

Figure 6:
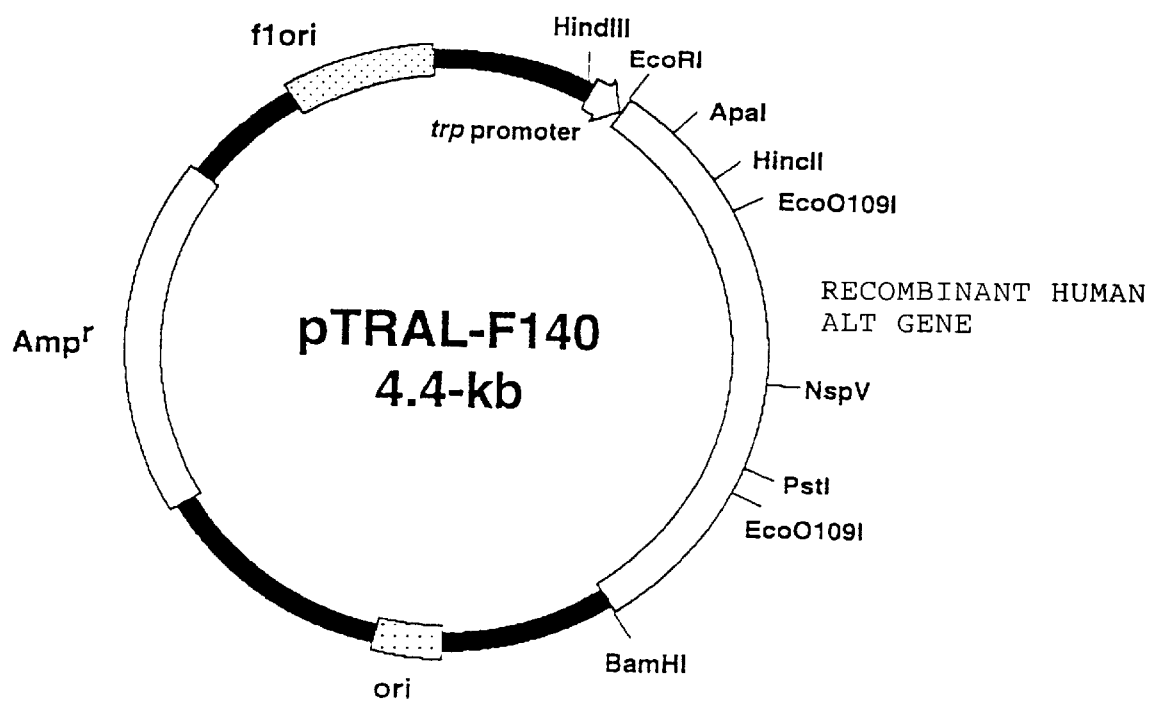
FIG. 6 shows recombinant plasmid pTRAL-F140.
Figure 7:
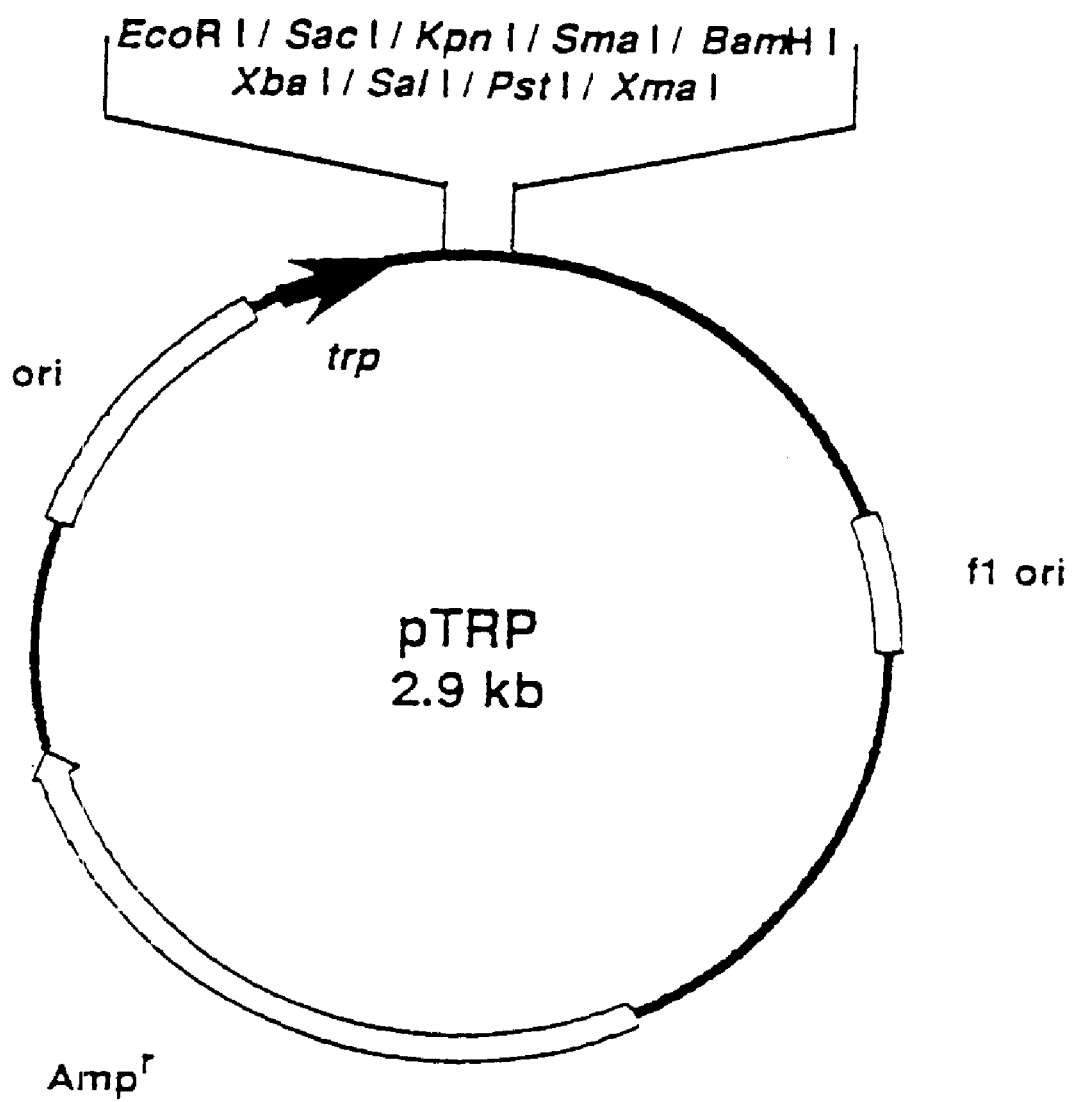
FIG. 7 shows expression vector pTRP.

Two gene fragments, i. e. PF21/PFA-21 and PF31/PFA-41, were concurrently introduced into cloning vector PTZ18U (manufactured by Pharmacia) digested in advance with EcoRI-BamHI and subcloned. A partial fragment (1.1 kb) of the ALT gene formed by digesting the obtained plasmid with EcoO109I-BamHI and a partial fragment (393 bp) of the ALT gene formed by digesting pHGT-F110 with restriction enzymes EcoRI-EcoO109I were mixed with an expression vector pTRP (2.9 kb) digested with EcoRI-BamHI, and ligated with the same ligation kit to give recombinant plasmid pTRAL-F140 (4.4 kb) containing the human ALT gene, in which five amino acids were replaced. Then, *Escherichia coli* MV 1190 strain was transformed with this reaction solution according to the TSS (Transformation Storage Solution) method (Proc. Natl. Acad. Sci. USA, 86, 2172–2175, 1989). An Ampicillin resistant strain was cultured that emerged in LB agar medium (a medium (pH 7.4) prepared by dissolving 10 g of tryptone (manufactured by Difco), 5 g of yeast extract (manufactured by Difco), 10 g of NaCl and 15 g of powdered agar in 1l of distilled water) containing 50 µg/ml of Ampicillin. A plasmid DNA was prepared by the method of Bimboim, Dolyetal (NucleicAcids Res., 7, 1513–1523, 1979), cut with EcoRI and BamHI and then the fact was confirmed by agarose gel electrophoresis that 1.5 kb altered-type human ALT gene was correctly inserted into the expression vector pTRP. The process for preparing recombinant plasmid pTRAL-F140 is shown in FIG. 5, and the structure of the obtained plasmid pTRAL-F140 is shown in FIG. 6. The structure of expression vector pTRP is shown in FIG. 7, and the total nucleotide sequence thereof is shown in FIG. 8 and FIG. 9.

(c) Expression of the Recombinant Active Human ALT in *Escherichia coli*

Recombinant plasmid pTRAL-F140 prepared by the process shown in (b) was introduced into *Escherichia coli* MV1190 strain according to the TSS method and the analysis of the human ALT expressed by the obtained transformed *Escherichia coli* MV1190 (pTRAL-F140) was preformed as follows. The obtained transformed microbe was named *Escherichia coli* MV1190 (pTRAL-F140) and deposited under the Budapest Treaty in the National Institute of Bioscience and Human-Technology, Agency of Industrial Science and Technology, 1-3, Higashi 1 chome, Tsukuba-shi, Ibaraki-ken, Japan, under an accession number FERM BP-5781 as the international deposit on January 8, 1997.

Transformed *Escherichia coli* MV1190 (pTRAL-F140) (FERM BP-5781) was inoculated in 200 ml of LB liquid medium, and after 18 hours at 30° C., when the culture reached the late stage of logarithmic growth phase, the microbe was transferred to 14 l of LB liquid medium. Similarly, after 18 hours at 30° C., when the culture reached the late stage of logarithmic growth phase, the cells were collected by centrifugation (10,000 ×g, 10 minutes). In 135 ml of Buffer A (40 mM acetate buffer (pH 5.5) containing 1 mM DTT, 1 mM EDTA, 5 mM 2-oxoglutarate and 50 µM pyridoxal phosphate) was suspended 27 g of the obtained wet cells. All the following operations were carried out at 4° C. After disrupting the cells by ultra-sonication, a cell-free extract was prepared by centrifugation (10,000 ×g, 10 minutes)

The cell-free extract was assayed for ALT activity and it was found that it has an activity of 1.58 U/mg protein. On the other hand, no ALT activity was found in the case of *Escherichia coli* host MV 1190, and accordingly, it could be confirmed that the activity detected in the transformed MV 1190 (pTRAL-F140) was derived from the recombinant human ALT.

Further, to 10 µl of this cell-free extract was added two times the volume of a sample treating solution (50 mM Tris-HCl (pH 6.8), 6% SDS, 20% glycerol, 200 mM dithiothreitol and 3mM phenylmethanesulfonyl fluoride (PMSF)). The mixture was heated at 60° C. for 30 minutes and subjected to SDS-polyacrylamide gel electrophoresis according to the method of Laemmli et al (Nature, 227, 680–685, 1970). After migration, the gel was stained with Coomassie Brilliant Blue R-250. As the result, a band of the human ALT at a molecular weight of about 55 k was detected, and further, this protein band showed a specific cross-reaction with anti-human ALT antibody. Accordingly, it was confirmed that the recombinant *Escherichia coli* MV 1190 (pTRAL-F140) effectively expressed the transformed human ALT as an active enzyme.

(d) Purification of the Recombinant Active Human ALT

In 135 ml of Buffer A (40 mM acetate buffer (pH 5.5) containing 1 mM DTT, 1 mM EDTA, 5 mM 2-oxoglutarate and 50 µM pyridoxal phosphate) was suspended 27 g of the wet cells of MV 1190 (pTRAL-F140). All the following operations were carried out at 4° C. After disrupting the cells by ultra-sonication, precipitate was removed by centrifugation (10,000 ×g, 10 minutes) to give a cell-free extract. To the extract (145 ml) was added 16.5 g of ammonium sulfate (20% saturation) and the mixture was stirred for 1.5 hour. After centrifugation (10,000 ×g, 10 minutes), 27.8 g of ammonium sulfate (50% saturation) was added to the obtained supernatant (147 ml) and the mixture was stirred for 1 hour. Precipitate under 20–50% saturation containing ALT activity was recovered by centrifugation (10,000 ×g, 10 minutes). In 33.4 ml of Buffer A was suspended the precipitate and the mixture was dialyzed against the same buffer for 15hours. After bringing the volume to 83.5 ml by addition of Buffer A, 12 g of ammonium sulfate (25% saturation) was added to the mixture, which was stirred for 1 hour and centrifuged (10,000 ×g, 10 minutes) to give a supernatant. The supernatant was applied onto Butyl-Toyopearl 650M (2.6×30 cm) (manufactured by Tosoh) equilibrated with Buffer Acontaining1.09Mammoniumsulfate. After washing with Buffer A containing 1.09 M ammonium sulfate, the recombinant h-ALT (human ALT) was eluted with a linear gradient of 1.09 M - 0 M ammonium sulfate.

The obtained active fraction was dialyzed against Buffer A for 15 hours and then applied onto CM-Sepharose CL6B (2.6×5 cm) (manufactured by Pharmacia) equilibrated with Buffer A. After washing with Buffer A containing 100 mM NaCl, the ALT was eluted with a linear gradient of 100–200 mM NaCl to give 5.45 mg protein of purified recombinant h-ALT. Its specific activity was 277 U/mg protein. As the result of SDS-polyacrylamide gel electrophoresis conducted with 1 µg of the purified preparation and staining with Coomassie Brilliant Blue R-250, only a band corresponding to the recombinant human ALT was confirmed.

(e) Comparison of the Obtained Human ALT

Properties of the recombinant active human ALT (altered ALT) obtained in this manner and those of non-altered ALT were compared as follows.

i) Difference in Translated Amino Acid Sequences

Five amino acid residues were different before and after the alteration. The amino acid sequence translated from the ALT gene after alteration was identical to the amino acid sequence, analyzed with a protein sequencer, of the native ALT purified from the human liver by Ishiguro et al. (Ishiguro et al., (1991), Biochemistry, 30, 10451–10457).

ii) Difference in Specific Activity

As described above, it was confirmed that the recombinant *Escherichia coli* MV 1190 (pTRAL-F140) effectively expressed the recombinant human ALT as an active enzyme. Although the amount of expression as a protein was not different before and after the alteration, the ALT activity in the crude cell extract was 1.58 U/mg protein after alteration as compared with 0.174 U/mg protein before alteration. When the comparison was made on the purified preparations, the activity was 277 U/mg protein after alteration as compared with 34.5 U/mg protein before alteration. Thus, it was confirmed that the ALT after alteration had a higher specific activity.

iii) Difference in Km Value

|  | L-alanine | 2-oxoglutaric acid |
|---|---|---|
| Before alteration | 83.3 mM | 6.99 mM |
| After alteration | 20.5 mM | 0.443 mM |

While the ALT before alteration had Km values for L-alanine and 2-oxoglutaric acid as the substrates quite different from those of the native ALT, the ALT after alteration had the same values as those of the native ALT.

iv) Difference in Isoelectric Point

When isoelectric point (pI) of ALT was measured by conducting electric focusing, it was found that the ALT before alteration had a pI of about 7.6 and the ALT after alteration had a pI of about 6.5. These values of isoelectric point roughly agreed with values estimated from the amino acid sequences. The pI value for the ALT after alteration was close to the pI value for the native ALT reported by Kanemitsu et al. (Kanemitsu, F. et al., Clin. Biochem., 23, 121–125, 1990).

By altering the human ALT gene to a nucleotide sequence encoding an amino acid sequence in which five amino acid residues are replaced through PCR and putting the altered gene under control of tryptophan promoter, the recombinant plasmid of the present invention can effectively express the recombinant human ALT as an active enzyme in the cells of *Escherichia coli*. Further, the obtained recombinant human ALT is the same as the naturally occurring ALT derived from the human liver and can be utilized, after purification, as the standard sample in serum diagnosis for exactly determining the amount of ALT leaked into serum in liver diseases.

Reference to Deposited Microorganism under Rule 13, bis

1. *Escherichia coli* MV1190 (pTRAL-F140)

A. Name and address of the depository institution in which said microorganism has been deposited:

Name: National Institute of Bioscience and Human-Technology, Agency of Industrial Science and Technology, Ministry of International Trade and Industry Address: 1-3, Higashi 1-Chome, Tsukuba-shi, Ibaraki-ken 305, Japan B. Date of deposition in the depository institution in A. Jan. 8, 1997

C. Accession number given to the deposit by the depository institution in A.

FERM BP-5781

What is claimed is:

1. An isolated DNA molecule, comprising the nucleotide sequence from nucleotides 9 to 1499 of SEQ ID NO:1.

2. The isolated DNA molecule according to claim 1, wherein restriction sites are linked to the sequence of nucleotides 9 to 1499 of SEQ ID NO:1 at the initiation end and the terminal end thereof.

3. The isolated DNA molecule according to claim 1, which comprises the nucleotide sequence from nucleotides 1 to 1505 of SEQ ID NO:1.

4. A recombinant plasmid in which the DNA molecule according to claim 2 is inserted into a vector plasmid.

5. An *Escherichia coli* host cell transformed with the recombinant plasmid of claim 4.

6. A process for producing an active human alanine aminotransferase (ALT), comprising:
cultivating the transformed *Escherichia coli* host cell of claim 5 in a culture medium; and
recovering ALT from the resultant cells thereof.

7. A recombinant plasmid in which the DNA molecule according to claim 3 is inserted into a vector plasmid.

8. An *Escherichia coli* host cell transformed with the recombinant plasmid according to claim 7.

9. A process for producing an active alanine aminotransferase (ALT), comprising:
cultivating the transformed Escherichia coli host cell of claim 8 in a culture medium; and
recovering ALT from the resultant cells thereof.

10. Recombinant plasmid pTRAL-F140.

11. An *Escherichia coli* host cell transformed with the recombinant plasmid of claim 10.

12. A process for producing an active alanine aminotransferase (ALT), comprising:
cultivating the transformed *Escherichia coli* host cell of claim 11 in a culture medium; and
recovering ALT from the resultant cells thereof.

13. A biologically pure culture of *Escherichia coli* MV1190 (pTRAL-F140), FERM BP-5781.

14. A process for producing an active alanine aminotransferase (ALT), comprising:
cultivating *Escherichia coli* MV1190 (pTRAL-F140), FERM BP-5781, of claim 13 in a culture medium; and
recovering ALT from the resultant cells thereof.

* * * * *

SEQUENCE LISTING

```
<160> NUMBER OF SEQ ID NOS: 14

<210> SEQ ID NO 1
<211> LENGTH: 1505
<212> TYPE: DNA
<213> ORGANISM: Homo sapiens
<220> FEATURE:
<221> NAME/KEY: CDS
<222> LOCATION: (9)..(1496)

<400> SEQUENCE: 1 gaattcat atg gca agc tca aca ggt gat aga tct cag gcg gtg agg cat       50
        Met Ala Ser Ser Thr Gly Asp Arg Ser Gln Ala Val Arg His
          1               5                  10 gga ctg agg gcg aag gtg ctg acg ctg gac ggc atg aac ccg cgt gtg        98
Gly Leu Arg Ala Lys Val Leu Thr Leu Asp Gly Met Asn Pro Arg Val
 15                  20                  25                  30 cgg aga gtg gag tac gca gtg cgt ggg ccc ata gtg cag cga gcc ttg       146
Arg Arg Val Glu Tyr Ala Val Arg Gly Pro Ile Val Gln Arg Ala Leu
                 35                  40                  45 gag ctg gag cag gag ctg cgc cag ggt gtg aag aag cct ttc acc gag       194
Glu Leu Glu Gln Glu Leu Arg Gln Gly Val Lys Lys Pro Phe Thr Glu
             50                  55                  60 gtc atc cgt gcc aac atc ggg gac gca cag gct atg ggg cag agg ccc       242
Val Ile Arg Ala Asn Ile Gly Asp Ala Gln Ala Met Gly Gln Arg Pro
```

-continued

```
             65                      70                      75
atc acc ttc ctg cgc cag gtc ttg gcc ctc tgt gtt aac cct gat ctt     290
Ile Thr Phe Leu Arg Gln Val Leu Ala Leu Cys Val Asn Pro Asp Leu
         80                      85                      90 ctg agc agc ccc aac ttc cct gac gat gcc aag aaa agg gcg gag cgc     338
Leu Ser Ser Pro Asn Phe Pro Asp Asp Ala Lys Lys Arg Ala Glu Arg
 95                     100                     105             110 atc ttg cag gcg tgt ggg ggc cac agt ctg ggg gcc tac agc gtc agc     386
Ile Leu Gln Ala Cys Gly Gly His Ser Leu Gly Ala Tyr Ser Val Ser
                    115                     120                     125 tcc ggc atc cag ctg atc cgg gag gac gtg gcg cgg tac att gag agg     434
Ser Gly Ile Gln Leu Ile Arg Glu Asp Val Ala Arg Tyr Ile Glu Arg
                130                     135                     140 cgt gac gga ggc atc cct gcg gac ccc aac aac gtc ttc ctg tcc aca     482
Arg Asp Gly Gly Ile Pro Ala Asp Pro Asn Asn Val Phe Leu Ser Thr
            145                     150                     155 ggg gcc agc gat gcc atc gtg acg gtg ctg aag ctg ctg gtg gcc ggc     530
Gly Ala Ser Asp Ala Ile Val Thr Val Leu Lys Leu Leu Val Ala Gly
        160                     165                     170 gag ggc cac aca cgc acg ggt gtg ctc atc ccc atc ccc cag tac cca     578
Glu Gly His Thr Arg Thr Gly Val Leu Ile Pro Ile Pro Gln Tyr Pro
175                     180                     185                     190 ctc tac tcg gcc acg ctg gca gag ctg ggc gca gtg cag gtg gat tac     626
Leu Tyr Ser Ala Thr Leu Ala Glu Leu Gly Ala Val Gln Val Asp Tyr
                    195                     200                     205 tac ctg gac gag gag cgt gcc tgg gcg ctg gac gtg gcc gag ctt gct     674
Tyr Leu Asp Glu Glu Arg Ala Trp Ala Leu Asp Val Ala Glu Leu Ala
                210                     215                     220 agg gct ctg ggc cag gcg cgt gac cac tgc cgc cct cgt gcg ctc tgt     722
Arg Ala Leu Gly Gln Ala Arg Asp His Cys Arg Pro Arg Ala Leu Cys
            225                     230                     235 gtc atc aac cct ggc aac ccc acc ggg cag gtg cag acc cgc gag tgc     770
Val Ile Asn Pro Gly Asn Pro Thr Gly Gln Val Gln Thr Arg Glu Cys
        240                     245                     250 atc gag gcc gtg atc cgc ttc gcc ttc gaa gag cgg ctc ttt ctg ctg     818
Ile Glu Ala Val Ile Arg Phe Ala Phe Glu Glu Arg Leu Phe Leu Leu
255                     260                     265                     270 gcg gac gag gtg tac cag gac aac gtg tac gcc gcg ggt tcg cag ttc     866
Ala Asp Glu Val Tyr Gln Asp Asn Val Tyr Ala Ala Gly Ser Gln Phe
                    275                     280                     285 cac tca ttc aag aag gtg ctc atg gag atg ggg ccg ccc tac gcc ggg     914
His Ser Phe Lys Lys Val Leu Met Glu Met Gly Pro Pro Tyr Ala Gly
                290                     295                     300 cag cag gag ctt gcc tcc ttc cac tcc acc tcc aaa ggc tac atg ggc     962
Gln Gln Glu Leu Ala Ser Phe His Ser Thr Ser Lys Gly Tyr Met Gly
            305                     310                     315 gag tgc ggg ttc cgc ggc ggc tat gtg gag gtg gtg aac atg gac gct    1010
Glu Cys Gly Phe Arg Gly Gly Tyr Val Glu Val Val Asn Met Asp Ala
        320                     325                     330 gca gtg cag cag cag atg ctg aag ctg atg agt gtg cgg ctg tgc ccg    1058
Ala Val Gln Gln Gln Met Leu Lys Leu Met Ser Val Arg Leu Cys Pro
335                     340                     345                     350 ccg gtg cca gga cag gcc ctg ctg gac ctg gtg gtc agc ccg ccc gcg    1106
Pro Val Pro Gly Gln Ala Leu Leu Asp Leu Val Val Ser Pro Pro Ala
                    355                     360                     365 ccc acc gac ccc tcc ttt gcg cag ttc cag gct gag aag cag gca gtg    1154
Pro Thr Asp Pro Ser Phe Ala Gln Phe Gln Ala Glu Lys Gln Ala Val
                370                     375                     380 ctg gca gag ctg gcg gcc aag gcc aag ctc acc gag cag gtc ttc aat    1202
```

```
Leu Ala Glu Leu Ala Ala Lys Ala Lys Leu Thr Glu Gln Val Phe Asn
        385                 390                 395 gag gct cct ggc atc agc tgc aac cca gtg cag ggc gcc atg tac tcc      1250
Glu Ala Pro Gly Ile Ser Cys Asn Pro Val Gln Gly Ala Met Tyr Ser
    400                 405                 410 ttc ccg cgc gtg cag ctg ccc ccg cgg gcg gtg gag cgc gct cag gag      1298
Phe Pro Arg Val Gln Leu Pro Pro Arg Ala Val Glu Arg Ala Gln Glu
415                 420                 425                 430 ctg ggc ctg gcc ccc gat atg ttc ttc tgc ctg cgc ctc ctg gag gag      1346
Leu Gly Leu Ala Pro Asp Met Phe Phe Cys Leu Arg Leu Leu Glu Glu
                435                 440                 445 acc ggc atc tgc gtg gtg cca ggg agc ggc ttt ggg cag cgg gaa ggc      1394
Thr Gly Ile Cys Val Val Pro Gly Ser Gly Phe Gly Gln Arg Glu Gly
            450                 455                 460 acc tac cac ttc cgg atg acc att ctg ccc ccc ttg gag aaa ctg cgg      1442
Thr Tyr His Phe Arg Met Thr Ile Leu Pro Pro Leu Glu Lys Leu Arg
        465                 470                 475 ctg ctg ctg gag aag ctg agc agg ttc cat gcc aag ttc acc ctc gag      1490
Leu Leu Leu Glu Lys Leu Ser Arg Phe His Ala Lys Phe Thr Leu Glu
    480                 485                 490 tac tcc tgaggatcc                                                    1505
Tyr Ser
495

<210> SEQ ID NO 2
<211> LENGTH: 496
<212> TYPE: PRT
<213> ORGANISM: Homo sapiens

<400> SEQUENCE: 2

Met Ala Ser Ser Thr Gly Asp Arg Ser Gln Ala Val Arg His Gly Leu
  1               5                  10                  15

Arg Ala Lys Val Leu Thr Leu Asp Gly Met Asn Pro Arg Val Arg Arg
                 20                  25                  30

Val Glu Tyr Ala Val Arg Gly Pro Ile Val Gln Arg Ala Leu Glu Leu
             35                  40                  45

Glu Gln Glu Leu Arg Gln Gly Val Lys Lys Pro Phe Thr Glu Val Ile
         50                  55                  60

Arg Ala Asn Ile Gly Asp Ala Gln Ala Met Gly Gln Arg Pro Ile Thr
 65                  70                  75                  80

Phe Leu Arg Gln Val Leu Ala Leu Cys Val Asn Pro Asp Leu Leu Ser
                 85                  90                  95

Ser Pro Asn Phe Pro Asp Asp Ala Lys Lys Arg Ala Glu Arg Ile Leu
                100                 105                 110

Gln Ala Cys Gly Gly His Ser Leu Gly Ala Tyr Ser Val Ser Ser Gly
            115                 120                 125

Ile Gln Leu Ile Arg Glu Asp Val Ala Arg Tyr Ile Glu Arg Arg Asp
        130                 135                 140

Gly Gly Ile Pro Ala Asp Pro Asn Asn Val Phe Leu Ser Thr Gly Ala
145                 150                 155                 160

Ser Asp Ala Ile Val Thr Val Leu Lys Leu Leu Val Ala Gly Glu Gly
                165                 170                 175

His Thr Arg Thr Gly Val Leu Ile Pro Ile Pro Gln Tyr Pro Leu Tyr
            180                 185                 190

Ser Ala Thr Leu Ala Glu Leu Gly Ala Val Gln Val Asp Tyr Tyr Leu
        195                 200                 205

Asp Glu Glu Arg Ala Trp Ala Leu Asp Val Ala Glu Leu Ala Arg Ala
```

-continued

| | 210 | | | 215 | | | | 220 | | | |
|---|---|---|---|---|---|---|---|---|---|---|---|
| Leu | Gly | Gln | Ala | Arg | Asp | His | Cys | Arg | Pro | Arg | Ala | Leu | Cys | Val | Ile |
| 225 | | | | | 230 | | | | 235 | | | | | | 240 |

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Arg Leu Phe Leu Leu Ala Asp
            260                 265                 270

Glu Val Tyr Gln Asp Asn Val Tyr Ala Ala Gly Ser Gln Phe His Ser
        275                 280                 285

Phe Lys Lys Val Leu Met Glu Met Gly Pro Pro Tyr Ala Gly Gln Gln
290                 295                 300

Glu Leu Ala Ser Phe His Ser Thr Ser Lys Gly Tyr Met Gly Glu Cys
305                 310                 315                 320

Gly Phe Arg Gly Gly Tyr Val Glu Val Asn Met Asp Ala Ala Val
                325                 330                 335

Gln Gln Gln Met Leu Lys Leu Met Ser Val Arg Leu Cys Pro Pro Val
                340                 345                 350

Pro Gly Gln Ala Leu Leu Asp Leu Val Val Ser Pro Pro Ala Pro Thr
            355                 360                 365

Asp Pro Ser Phe Ala Gln Phe Gln Ala Glu Lys Gln Ala Val Leu Ala
370                 375                 380

Glu Leu Ala Ala Lys Ala Lys Leu Thr Glu Gln Val Phe Asn Glu Ala
385                 390                 395                 400

Pro Gly Ile Ser Cys Asn Pro Val Gln Gly Ala Met Tyr Ser Phe Pro
                405                 410                 415

Arg Val Gln Leu Pro Pro Arg Ala Val Glu Arg Ala Gln Glu Leu Gly
            420                 425                 430

Leu Ala Pro Asp Met Phe Phe Cys Leu Arg Leu Leu Glu Glu Thr Gly
            435                 440                 445

Ile Cys Val Val Pro Gly Ser Gly Phe Gly Gln Arg Glu Gly Thr Tyr
            450                 455                 460

His Phe Arg Met Thr Ile Leu Pro Pro Leu Glu Lys Leu Arg Leu Leu
465                 470                 475                 480

Leu Glu Lys Leu Ser Arg Phe His Ala Lys Phe Thr Leu Glu Tyr Ser
                485                 490                 495

<210> SEQ ID NO 3
<211> LENGTH: 54
<212> TYPE: DNA
<213> ORGANISM: Homo sapiens
<220> FEATURE:
<221> NAME/KEY: CDS
<222> LOCATION: (11)..(52)

<400> SEQUENCE: 3
gggaattcat atg gca agc tca aca ggt gat aga tct cag gcg gtg agg         49
            Met Ala Ser Ser Thr Gly Asp Arg Ser Gln Ala Val Arg
              1               5                  10 cat gg                                                                  54
His

<210> SEQ ID NO 4
<211> LENGTH: 14
<212> TYPE: PRT
<213> ORGANISM: Homo sapiens

<400> SEQUENCE: 4

Met Ala Ser Ser Thr Gly Asp Arg Ser Gln Ala Val Arg His
 1               5                  10

<210> SEQ ID NO 5
<211> LENGTH: 26
<212> TYPE: DNA
<213> ORGANISM: Homo sapiens

<400> SEQUENCE: 5
tatgggccca cgcactgcgt actcca                                          26

<210> SEQ ID NO 6
<211> LENGTH: 8
<212> TYPE: PRT
<213> ORGANISM: Homo sapiens

<400> SEQUENCE: 6

Glu Tyr Ala Val Arg Gly Pro Ile
 1               5

<210> SEQ ID NO 7
<211> LENGTH: 27
<212> TYPE: DNA
<213> ORGANISM: Homo sapiens

<400> SEQUENCE: 7
cgtgggccca tagtgcagcg agccttg                                         27

<210> SEQ ID NO 8
<211> LENGTH: 22
<212> TYPE: DNA
<213> ORGANISM: Homo sapiens

<400> SEQUENCE: 8
ttggcatcgt cagggaagtt gg                                              22

<210> SEQ ID NO 9
<211> LENGTH: 30
<212> TYPE: DNA
<213> ORGANISM: Homo sapiens

<400> SEQUENCE: 9
ctggaattcc ccaacttccc tgacgatgcc                                      30

<210> SEQ ID NO 10
<211> LENGTH: 33
<212> TYPE: DNA
<213> ORGANISM: Homo sapiens

<400> SEQUENCE: 10
cagaggccta gcaagctcgg ccacgtccag cgc                                  33

<210> SEQ ID NO 11
<211> LENGTH: 9
<212> TYPE: PRT
<213> ORGANISM: Homo sapiens

<400> SEQUENCE: 11

Ala Leu Asp Val Ala Glu Leu Ala Arg
 1               5

<210> SEQ ID NO 12
<211> LENGTH: 27
<212> TYPE: DNA

<210> SEQ ID NO 13
<211> LENGTH: 42
<212> TYPE: DNA
<213> ORGANISM: Homo sapiens

<400> SEQUENCE: 13

```
ggggatcctc aggagtactc gagggtgaac ttggcatgga ac                42
```

<210> SEQ ID NO 14
<211> LENGTH: 2927
<212> TYPE: DNA
<213> ORGANISM: Artificial Sequence
<220> FEATURE:
<223> OTHER INFORMATION: Description of Artificial Sequence: Hybrid of
      human and artificial vector sequences

<400> SEQUENCE: 14

```
agcgcccaat acgcaaaccg cctctcccccg cgcgttggcc gattcattaa tgcagctggc    60
acgacaggtt tcccgactgg aaagcgggca gtgagcgcaa cgcaattaat gtgagttagc   120
tcactcatta ggcaccccag gctttacact ttatgcttcc ggctcgtatg ttgtgtggaa   180
ttgtgagcgg ataacaattt cacacaggaa acagctatga ccatgattac gccaagctct   240
aatacgactc actatagggg aagcttccct gttgacaatt aatcatcgaa ctagttaaca   300
gtacgcaagt tcacgtaaaa agggtagaat tcgagctcgg tacccgggga tcctctagag   360
tcgacctgca ggtcgaaatt cactggccgt cgttttacaa cgtcgtgact gggaaaaccc   420
tggcgttacc caacttaatc gccttgcagc acatccccct ttcgccagct ggcgtaatag   480
cgaagaggcc cgcaccgatc gcccttccca acagttgcgc agcctgaatg gcgaatggga   540
cgcgccctgt agcggcgcat taagcgcggc gggtgtggtg gttacgcgca gcgtgaccgc   600
tacacttgcc agcgccctac cgcccgctcc tttcgctttc ttcccttcct ttctcgccac   660
gttcgccggc tttccccgtc aagctctaaa tcggggggctc cctttagggt tccgatttag   720
tgctttacgg cacctcgacc ccaaaaaact tgattagggt gatggttcac gtagtgggcc   780
atcgccctga tagacggttt ttcgcccttt gacgttggag tccacgttct ttaatagtgg   840
actcttgttc caaactggaa caacactcaa ccctatctcg gtctattctt ttgatttata   900
agggattttg ccgatttcgg cctattggtt aaaaaatgag ctgatttaac aaaaatttaa   960
cgcgaatttt aacaaaatat taacgtttac aatttcaggt ggcactttc ggggaaatgt  1020
gcccggaacc cctatttgtt tatttttcta aatacattca aatatgtatc cgctcatgag  1080
acaataaccc tgataaatgc ttcaataata ttgaaaaagg aagagtatga gtattcaaca  1140
tttccgtgtc gcccttattc ccttttttgc ggcattttgc cttcctgttt ttgctcaccc  1200
agaaacgctg gtgaaactaa agatgctga agatcagttg ggtgcacgag tgggttacat  1260
cgaactggat ctcaacagcg gtaagatcct tgagagtttt cgccccgaag aacgttttcc  1320
aatgatgagc acttttaaag ttctgctatg tggcgcggta ttatcccgta ttgacgccgg  1380
gcaagagcaa ctcggtcgcc gcatacacta ttctcagaat gacttggttg agtactcacc  1440
agtcacagaa aagcatctta cggatggcat gacagtaaga gaattatgca gtgctgccat  1500
aaccatgagt gataacactg cggccaactt acttctgaca acgatcggag gaccgaagga  1560
```

-continued

```
gctaaccgct tttttgcaca acatggggga tcatgtaact cgccttgatc gttgggaacc    1620
ggagctgaat gaagccatac caaacgacga gcgtgacacc acgatgcctg tagcaatggc    1680
aacaacgttg cgcaaactat taactggcga actacttact ctagcttccc ggcaacaatt    1740
aatagactgg atggaggcgg ataaagttgc aggaccactt ctgcgctcgg cccttccggc    1800
tggctggttt attgctgata aatctggagc cggtgagcgt gggtctcgcg gtatcattgc    1860
agcactgggg ccagatggta agccctcccg tatcgtagtt atctacacga cggggagtca    1920
ggcaactatg gatgaacgaa atagacagat cgctgagata ggtgcctcac tgattaagca    1980
ttggtaactg tcagaccaag tttactcata tatactttag attgatttaa aacttcattt    2040
ttaatttaaa aggatctagg tgaagatcct ttttgataat ctcatgacca aaatccctta    2100
acgtgagttt tcgttccact gagcgtcaga ccccgtagaa aagatcaaag gatcttcttg    2160 agatccttt tttctgcgcg taatctgctg cttgcaaaca aaaaaccac cgctaccagc      2220 ggtggtttgt ttgccggatc aagagctacc aactcttttt ccgaaggtaa ctggcttcag    2280
cagagcgcag ataccaaata ctgtccttct agtgtagccg tagttaggcc accacttcaa    2340
gaactctgta gcaccgccta catacctcgc tctgctaatc ctgttaccag tggctgctgc    2400
cagtggcgat aagtcgtgtc ttaccgggtt ggactcaaga cgatagttac cggataaggc    2460
gcagcggtcg ggctgaacgg ggggttcgtg cacacagccc agcttggagc gaacgaccta    2520
caccgaactg agatacctac agcgtgagca ttgagaaagc gccacgcttc ccgaagggag    2580
aaaggcggac aggtatccgg taagcggcag ggtcggaaca ggagagcgca cgagggagct    2640
tccaggggga aacgcctggt atctttatag tcctgtcggg tttcgccacc tctgacttga    2700
gcgtcgattt ttgtgatgct cgtcaggggg gcggagccta tggaaaaacg ccagcaacgc    2760
ggccttttta cggttcctgg ccttttgctg gcctttttgct cacatgttct ttcctgcgtt   2820 atccctgat tctgtggata accgtattac cgccttgag tgagctgata ccgctcgccg     2880
cagccgaacg accgagcgca gcgagtcagt gagcgaggaa gcggaag                 2927
```